US007507183B2

(12) United States Patent
Anderson et al.

(10) Patent No.: US 7,507,183 B2
(45) Date of Patent: Mar. 24, 2009

(54) HEALTH CLUB EXERCISE RECORDS SYSTEM

(76) Inventors: Brent Anderson, 2047 Rose Pt. La., Kirkland, WA (US) 98033; Douglas E. Nichols, 20203 Marine View Dr. SW., Normandy Park, WA (US) 98166-4127

( * ) Notice: Subject to any disclaimer, the term of this patent is extended or adjusted under 35 U.S.C. 154(b) by 681 days.

(21) Appl. No.: 10/819,052

(22) Filed: Apr. 6, 2004

(65) Prior Publication Data
US 2004/0198555 A1    Oct. 7, 2004

Related U.S. Application Data

(60) Provisional application No. 60/461,204, filed on Apr. 7, 2003.

(51) Int. Cl.
*A63B 15/02* (2006.01)
(52) U.S. Cl. .................................. 482/1; 482/8; 482/9
(58) Field of Classification Search ................. 482/1–9, 482/900–902; 434/247; 601/23; 705/1–3
See application file for complete search history.

(56) References Cited

U.S. PATENT DOCUMENTS

| 4,283,712 | A | 8/1981 | Goody | 340/323 |
|---|---|---|---|---|
| 5,059,778 | A | 10/1991 | Zouzoulas et al. | 235/472 |
| 5,387,164 | A | 2/1995 | Brown, Jr. | 482/9 |
| 5,473,831 | A | 12/1995 | Locke | 40/490 |
| 5,474,090 | A | 12/1995 | Begun et al. | 128/707 |
| 5,478,295 | A | 12/1995 | Fracchia | 482/7 |
| 5,516,334 | A | 5/1996 | Easton | 482/8 |
| 5,598,849 | A | 2/1997 | Browne | 128/707 |
| 5,890,997 | A | 4/1999 | Roth | 482/8 |
| 5,944,633 | A | 8/1999 | Wittrock | 482/4 |
| 5,947,869 | A * | 9/1999 | Shea | 482/8 |
| 6,050,924 | A | 4/2000 | Shea | 482/57 |
| 6,244,988 | B1 | 6/2001 | Delman | 482/8 |

(Continued)

FOREIGN PATENT DOCUMENTS

WO    WO009626495 A1 *    8/1996

*Primary Examiner*—Glenn Richman
(74) *Attorney, Agent, or Firm*—Dean A. Craine

(57) ABSTRACT

A health club exercise records system in which members to the health club are given a handheld device that is pre-programmed by the trainer or health club operator to record different exercise activities. The handheld device includes a built-in numeric keypad, a display monitor, and optical reader designed to communicate with a compatible ID tag located on or in the vicinity of the exercise activity data source. Loaded into the working memory of the handheld device is a pre-programmed exercise data collection program. The exercise data collection program displays one or more sub-routines to the member requesting the member to input information regarding the exercise. The sub-routines are specific to the exercise activity data source and present one or more prompts requiring the member to input information. The inputted information is stored in a temporary data file located on the handheld device or transmitted immediately to a permanent member data file on a local server located in the health club. The system may also include an uplink terminal for transmitting the data in the temporarily data file to a remote server connected to a network operations center. A fitness tools software program is loaded into the server for collecting and processing the data in the member's permanent data file which may be reviewed by the trainer and/or member.

10 Claims, 5 Drawing Sheets

U.S. PATENT DOCUMENTS

| | | |
|---|---|---|
| 6,358,188 B1 | 3/2002 | Ben-Yehuda et al. ............ 482/8 |
| 6,588,670 B2 | 7/2003 | Bukowski |
| 6,702,719 B1 * | 3/2004 | Brown et al. ................... 482/8 |
| 6,793,607 B2 * | 9/2004 | Neil ................................ 482/8 |
| 6,796,927 B2 * | 9/2004 | Toyama ......................... 482/8 |
| 6,827,670 B1 * | 12/2004 | Stark et al. ..................... 482/9 |
| 7,056,265 B1 * | 6/2006 | Shea .............................. 482/8 |
| 2001/0053735 A1 * | 12/2001 | Cohen et al. ................ 482/902 |
| 2002/0086774 A1 * | 7/2002 | Warner .......................... 482/8 |
| 2003/0158014 A1 * | 8/2003 | Valentin-Sivico .............. 482/8 |
| 2003/0226695 A1 * | 12/2003 | Mault ...................... 177/25.16 |
| 2005/0064995 A1 * | 3/2005 | Shitan ........................... 482/8 |

* cited by examiner

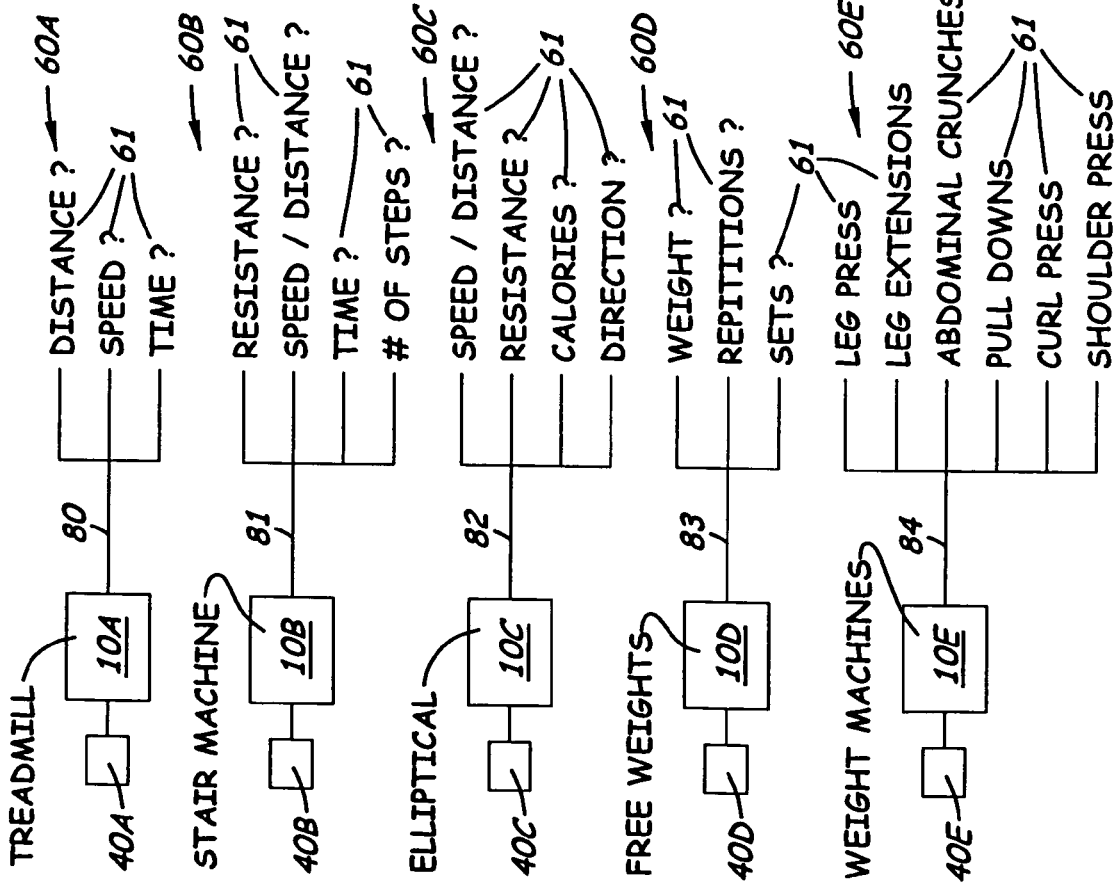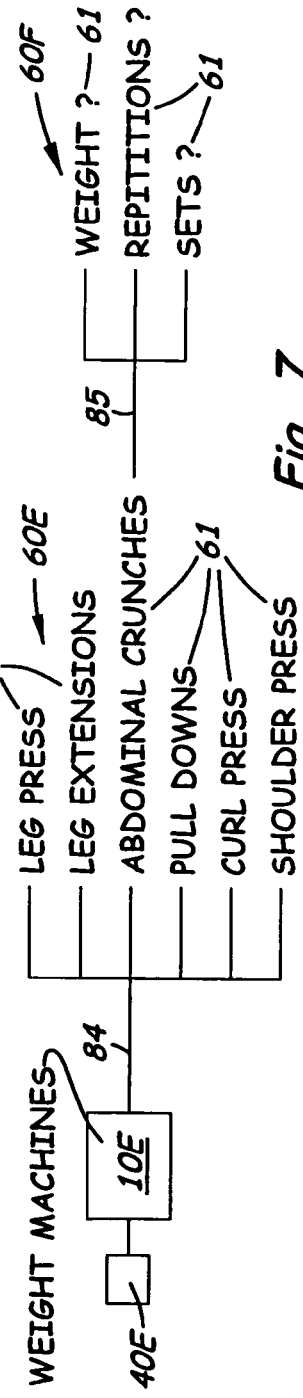

HEALTH CLUB EXERCISE RECORDS SYSTEM

This utility patent application is based on the provisional patent application (Ser. No. 60/461,204) filed on Apr. 7, 2003.

BACKGROUND OF THE INVENTION

1. Field of the Invention

This invention relates to exercise metrics recording systems, and more particularly, to exercise metrics recording systems located in health club/gym facilities that offer different pieces of exercise equipment and exercise activities to its members.

2. Description of the Related Art

There are approximately 22 thousand fitness centers and health clubs in the United States serving approximately 40 million members. The health club industry is characterized by rapid growth in club members (8% per annum) and an explosion in exercise related activities and equipment. There has also been tremendous growth in information related to the optimal use of exercise equipment including: the best use of time devoted to exercise, long term impact of specific exercise activity, avoidance of injury, and preferred combinations of exercises.

To help individual health club members maximize the benefit of time spent exercising, most health clubs offer professional training services. Professional training services support the goals of maximizing the benefit of time expended toward exercise, injury avoidance, and maintaining a long-term focus to a given exercise regime. Professional training services (as currently offered) require the trainer to directly participate in his or her clients' exercise sessions to observe and track activity and performance. Direct participation by the professional trainer in most or all of his or her clients' exercise sessions carries with it a number of negative attributes, including very high service costs, advance scheduling requirements for exercise sessions, regimentation of recreational workout activity into 'hard core' training sessions and, for some, a 'loss of privacy' in exercise activity that many health club members view negatively.

An effective exercise metrics recording system enabling individuals to independently record their exercise activity in a digital format would permit fitness professionals to effectively counsel and/or train the individual system member without necessitating the trainer's direct participation in each of the client's day to day workouts. Such an exercise metrics recording system would also eliminate advance scheduling and aesthetic problems associated with the use of professional training services. Most important, such an exercise metrics recording system would permit professional counseling services to be rendered more efficiently at prevailing price levels, and enable health clubs to provide a much broader range of fitness training/counseling services to address the needs and price constraints of the majority of health club members. Finally, the digital exercise and fitness records produced by such an exercise metrics recording system could be provided to third parties not affiliated with the health club or fitness center, such as doctors, therapists, managed healthcare providers, corporate wellness program administrators, etc., who have an interest in the health and well-being of particular health club members.

Two basic approaches have been attempted toward the goal of recording exercise activity onto a digital medium: "active network systems" and "scripted training systems."

Active network systems deploy a local electronic network in the health club with each exercise machine equipped with a display monitor, data input means and sensors, and operating as a data collection node. The health club member identifies himself or herself to a particular machine or workout station via an entry of a personal identification number on a key pad at the workout station. Upon completion of the exercise, certain performance information collected by sensors at the workout station is transmitted to a central server where individual exercise records are stored. Active network systems are effective where exercise equipment operates at a fixed location in the gym or fitness center, and where each piece of exercise equipment in the network supports only one or two exercise movements.

Active network systems encounter problems dealing with any equipment that is mobile or capable of being employed in multiplicities of exercise movements. Free weights are the most obvious example of exercise equipment that cannot be linked in an active network system. In addition to problems accommodating data input from some types of exercise equipment, active network systems do not support tracking of activity-related exercise (e.g., aerobic dancing; running; basketball; etc). Additionally, the provisioning of electrical power to active networked systems and the installation of network monitors, data input means, and sensors at each piece of the networked equipment result in high capital installation costs and high recurring maintenance costs. Active network systems are also costly to expand as new exercise machines and methods are brought into the health club.

The second means to record exercise-related activity involves the use of dedicated software programs operating on PDAs or similar handheld devices. Exercise software programs fall into two categories: "menu-driven database programs" and "scripted exercise routine systems."

Exercise menu-driven programs involve simple database lookup programs applied to the tracking of fitness activity. Using a PDA or similar handheld device, the health club member scrolls through a preprogrammed menu of commonly available exercises, identifies his or her intended exercise activity, and enters certain performance information into the handheld device upon completion of the exercise. The principal problem with menu-driven database programs as applied to health and fitness records is the length and complexity of the menu necessary to accommodate the literally thousands of exercise options available in a typical health club. The burden of cycling through available workout options to locate the desired entry point in the database program has rendered menu-driven database programs too burdensome for most health club members and impractical as effective exercise metrics tracking systems. U.S. Pat. Nos. 4,493,485; 4,409,992; 4,408,183; and 5,890,997.

Scripted exercise records systems exist in multiple forms. In their simplest embodiment, a piece of paper can be carried by a person through a workout session with an exercise program written on it. As the person follows the prescribed routine, he or she checks boxes and/or writes down performance data associated with each exercise completed. Systems have been developed to simplify the task of data entry and data conversion into a digital format by introducing a PDA or similar handheld device configured to store user exercise performance data relative to an exercise script which is carried on the PDA-like device or recorded on a workout card to be read by the PDA. There is any number of innovations relative to script-based exercise records systems, but the identification of these script-based exercise record systems as "related art" is problematic. Scripted systems simply do not meet the challenge of identifying what exercise activities a person elected to perform during a given workout session. Rather than address the multiple thousands of combinations related to exercise data sources and possible combinations of weight used, repetitions completed, elapsed time, distance, speed, resistance level, etc., scripted systems allow a user to record performance against a narrowly defined exercise program. The user performs the prescribed exercise and then records certain performance information by hand or into a PDA or similar handheld device, which contains the exercise script. The limitations placed on data input sources by script-based exercise records systems represent a fundamental difference relative to the subject invention and other "related art" described herein. Script-based exercise systems necessarily require users to strictly follow a prescribed training program in order to track performance. While most health club members follow generalized patterns in their exercise and recreation, the majority of health club members do not strictly follow training programs (the average health club member being over 30 years in age and more interested in maintaining a reasonable level of fitness and health rather than training for a marathon or engaging in "body sculpting"). Accordingly, script-based systems have enjoyed limited acceptance among health club members. Finally, while script-based systems are not precisely "related art," a second issue is worth noting that has kept such systems from enjoying wide application in the health and fitness club market.

An exercise script for a PDA can be written by anyone for use by a health club member in any gym. While the health club operator can control perimeter facility access, the health club operator cannot control access to individual exercise apparatus or compel the use of his or her club-based training services in conjunction with the script-based system. In fact, script-based exercise records systems operate to introduce internet-based and/or non-resident trainer competition into a health club, threatening a major revenue source for the typical health club. Consequently, script-based systems have been relegated to treatment related exercise programs (healthcare provider prescribed) with very limited acceptance by internet-based trainers.

A need exists for a new exercise metrics collection system for a health club capable of collecting, transferring, storing, and managing individual exercise records of its members, without the operating restrictions and high costs described herein above. The new system will differ from existing methods, offering its members easy and flexible operation unencumbered by scripted exercise routines which are directive in nature. Such a system should accept data input from any fitness data source including activity-based workouts (e.g., aerobic dancing; running; basketball; etc.), stretching, all forms of resistance training (including exercises using free-weights), and biometric monitoring devices. In addition, such a system should be materially less expensive to install and maintain than are active network systems, and must provide for owner control of access to the system in the facility in which it is installed, particularly its exercise identification component.

SUMMARY OF THE INVENTION

It is an object of the present invention to provide an inexpensive, easy to use exercise metrics records system specifically designed for use in a health club and other sports and fitness facilities which offers different pieces of exercise equipment and exercise activities to its members.

It is another object of the present invention to provide such a system that uses handheld devices that allow members to easily record various exercise activities in the health club.

It is another object of the present invention to provide such a system that provides exercise machine or exercise activity related sub-routines to the member that instructs the member regarding the type of data to be inputted into the handheld device by the member after the exercise is completed.

It is another object of the present invention to provide such a system that allows health club-based trainers the option to selectively program the handheld device for specific members instructing the members to include one or more specific types of exercise and the intensity level to be performed on those recommended exercises.

It is another object of the present invention to provide such a system that is relatively inexpensive to assemble, install and maintain.

It is another object of the present invention to provide such a system that uses only handheld devices that are uniquely configured and provided by the health club for use in the health club.

It is another object of the present invention to provide such a system that does not require the direct participation of a trainer during or after every exercise session.

It is another object of the present invention to provide such a system that does not require a member to perform exercise activity according to a prescribed sequence.

It is another object of the present invention to provide such a system that can be linked to other health clubs so that members' exercise records may be aggregated and quantitatively or qualitatively evaluated, and shared.

It is another object of the present invention to provide such a system that can centrally store, protect, and discretely distribute individual exercise records in such a way as to allow individual records to address member exercise activity performed away from the member's primary gym, and to allow for the distribution of individual exercise records to interested and authorized third parties (e.g., healthcare providers, weight-loss clinics, insurance providers, Department of Defense representatives in force-readiness applications.

It is another object of the present invention to provide such a system that can deploy statistical analysis techniques and database tools against a centrally stored collection of individual exercise records to provide business and public interest related data mining of the system's population of individual records.

It is another object of the present invention to provide such a system that deploys software tools which apply statistical analysis techniques and fitness related information and principles against an individual's particular exercise records to aid in maintaining safe and effective exercise patterns.

These objects are met by a health club exercise records system disclosed herein that enables health club members to easily record different exercise activities performed in health clubs and other sports and fitness facilities. The system includes a portable handheld device capable of being pre-programmed by the trainer for a specific member that is then used by the member to record exercise activities. The system also includes a unique identifying "exercise identification module", hereinafter referred to as an EIDM, attached to or located in the proximate vicinity of an exercise activity source. The EIDM is unique to the exercise data source it represents and to the facility in which the exercise data source resides. The EIDM is also capable of limiting the communication of its exercise data source identification information only to those handhelds authorized for use in the health club facility in which the EIDM resides. The handheld device includes a display monitor, a data input means, and an EIDM interrogation means used to query the EIDM. During use, the member activates the handheld device which executes an exercise data collection software program loaded into the working memory of the handheld device. When the member selects a piece of exercise equipment or an exercise activity (e.g. weight lifting), the EIDM interrogation means is activated and used to interrogate the EIDM. When the EIDM is identified, the exercise data collection software program automatically executes a software sub-routine specifically designed for the individual and/or the specific exercise activity source associated with the EIDM. More specifically, the sub-routine presents a data entry page on the display monitor. The data entry page identifies the exercise machine or activity, the type of exercise to be completed, and presents a plurality of prompts requesting specific information from the member regarding the exercise activity performed on the exercise activity data source. The information that is inputted into the handheld device using the input means is directly stored in a temporary member data file on the handheld device or transmitted directly to a permanent member data file stored on a local server located in the health club. If the information is stored in a temporary member data file on the handheld, it is later uploaded to the local server. Each time the member moves to a new exercise data activity source, the EIDM interrogation means and the EIDM are used to quickly identify the exercise activity data source and present the proper sub-routine associated with the exercise data activity source.

In the first embodiment, the system includes a local server located in the health club with permanent member data files that contains the inputted records from the handheld devices used by members in the health club. In another embodiment, the local server is replaced by an uplink terminal connected to a remote server located in a network operations center, hereinafter referred to as a NOC, via the Internet. In both embodiments, a database software program is included that is designed to collect the uploaded records in the handheld device's temporary member data file and then present the information to the trainer and/or member when connected to the central server. The system will also use a tool set of software programs accessible via personal computer, hereinafter referred to as a 'tool set', which supports data correlations unique to the science of health and fitness and associated directly or indirectly with the member's specific workout history. The system will cross-track and display to the health and fitness professional any number of relationships and data correlations associated with the member's various workout sessions. In addition, the tool set will maintain and display information to the fitness professional who is counseling the member, via state of the art graphical and visual representations, identifying areas of concern and/or progress which may suggest alternative courses of action in terms of exercise type and exercise intensity which the fitness professional recommends the member adopt in his or her exercise regime.

Using the above-described device, a method of recording the exercise routines in a health club is also provided. During use, the member selects a health club with different exercise activity data sources each associated with a unique EIDM. When the member visits the health club, he or she is provided a handheld device as describe above loaded with various software sub-routines associated with the EIDMs. As the member moves throughout the health club, he or she performs various exercise activities, and inputs data in response to the sub-routine prompts. When the exercise activity is completed, the temporary member data file on the handheld device is uploaded to the local server or to the remote server on the NOC. The fitness database software program on the local server or remote server is then used by the trainer to review a member's data file. The tool set provides the trainer access to the most recent information relative that member's exercise needs as well as a backup to the trainer's own record review, ensuring that all areas of concern have been identified and addressed by the trainer relative to the member.

The subject invention deploys an architecture which is unique and novel relative to the collection of individual workout information in a health club environment.

Unlike the prior art active network systems identified herein, the subject invention deploys a handheld device to collect individual exercise records; with this step the subject invention becomes an order of magnitude less expensive than active network systems to install, operate, and maintain. With the elimination of the active network approach, the subject invention becomes far more flexible in its operation, allowing the system to breakaway from fixed machine limitations of active network systems to embrace free weights, basketball, running, handball, and virtually any other exercise activity.

Deployment of a handheld device in the system, together with an EIDM with which the handheld shares a relationship in a site-unique database, and the location of that EIDM on or in close proximity to its represented exercise data source, allows the subject invention to gather data from anywhere in the health club, anytime, and in any sequence of use. In this manner, the subject invention enables the use of a handheld device for data collection without confining its user to a scripted workout, thereby allowing him or her to simply approach and query the EIDM for the exercise to be performed, rather than searching through multiple and lengthy software menus or similar hand-carried exercise reference material to effect the identification.

By employing unique identifiers for each exercise data source at a specific site, and by providing for encrypted query/response capability for each EIDM, access to the system can be restricted to authorized users. This access-control characteristic of the subject invention holds significant financial implications for owners and operators of the system disclosed herein.

The over-arching structure and individual elements deployed in the subject invention for the secure transfer and handling of data related to individual workout records ensures the capability for fitness professionals in the health club to provide effective counseling services to members using state of the art data analysis and presentation tools. Beyond counseling applications, the subject invention's network structure, user authentication functions, and records storage and manipulation capabilities will allow individual fitness records to be made available to authorized and interested third parties. In addition, the database of member activity and preferences accumulated via the system can be "mined" as a data resource for both public and private sector interests.

Importantly, at the core of the subject invention is a simple, flexible, easy to use, and inexpensive system which provides the means to eliminate the requirement for gym-based fitness professionals to participate directly in every member's workout in order to gain sufficient specific knowledge about the member's exercise patterns to effectively counsel the member.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in vari-

DESCRIPTION OF THE DRAWINGS

FIG. 6 is an illustration of an exercise data page shown on the display monitor.

FIG. 7 is an illustration of various exercise equipment showing different sub-routines executed to display different exercise data pages to the member.

DESCRIPTION OF THE PREFERRED EMBODIMENT(S)

Figure 1:
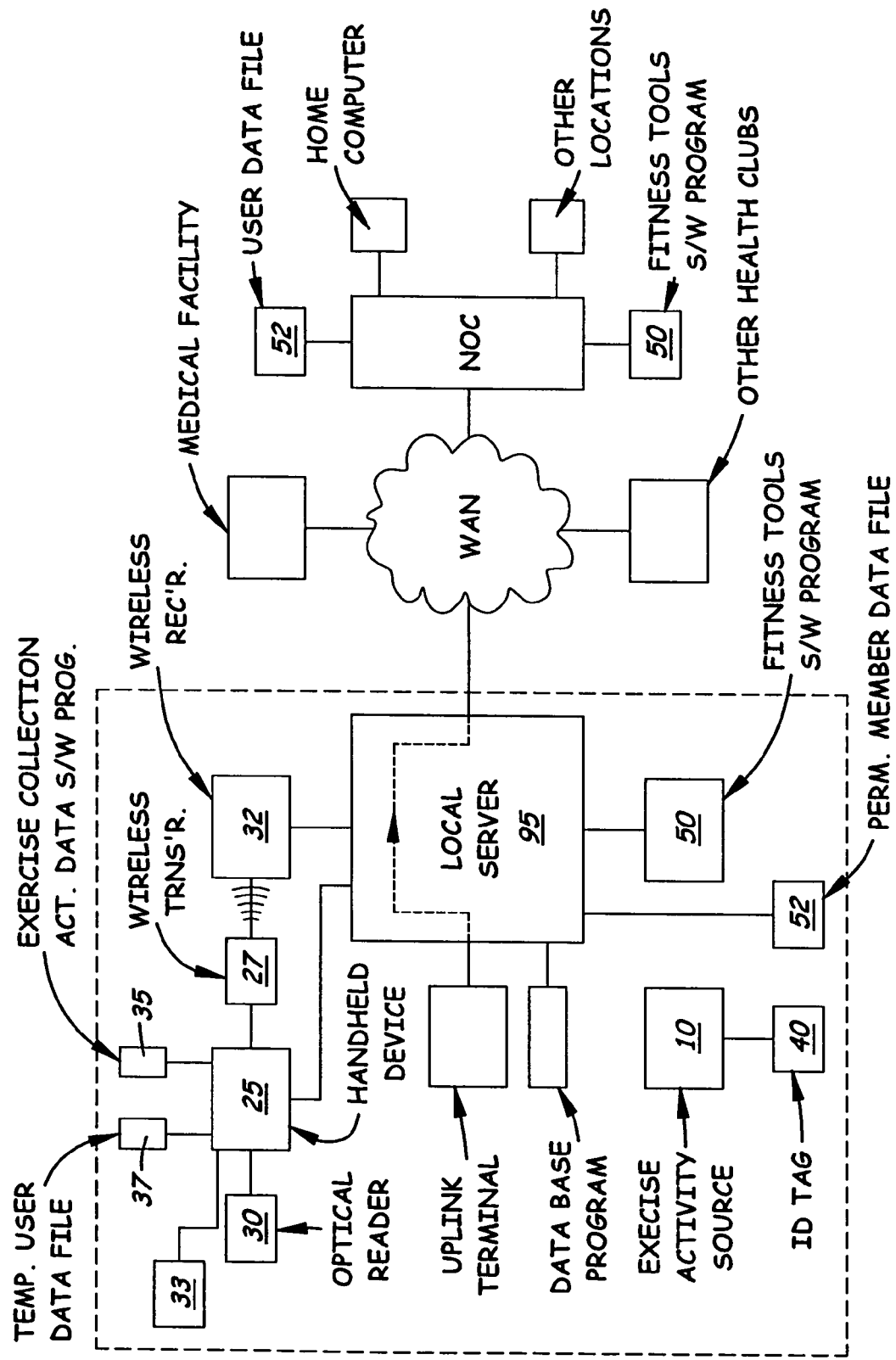
FIG. 1 is an illustration of the health club exercise records system.
Figure 2:
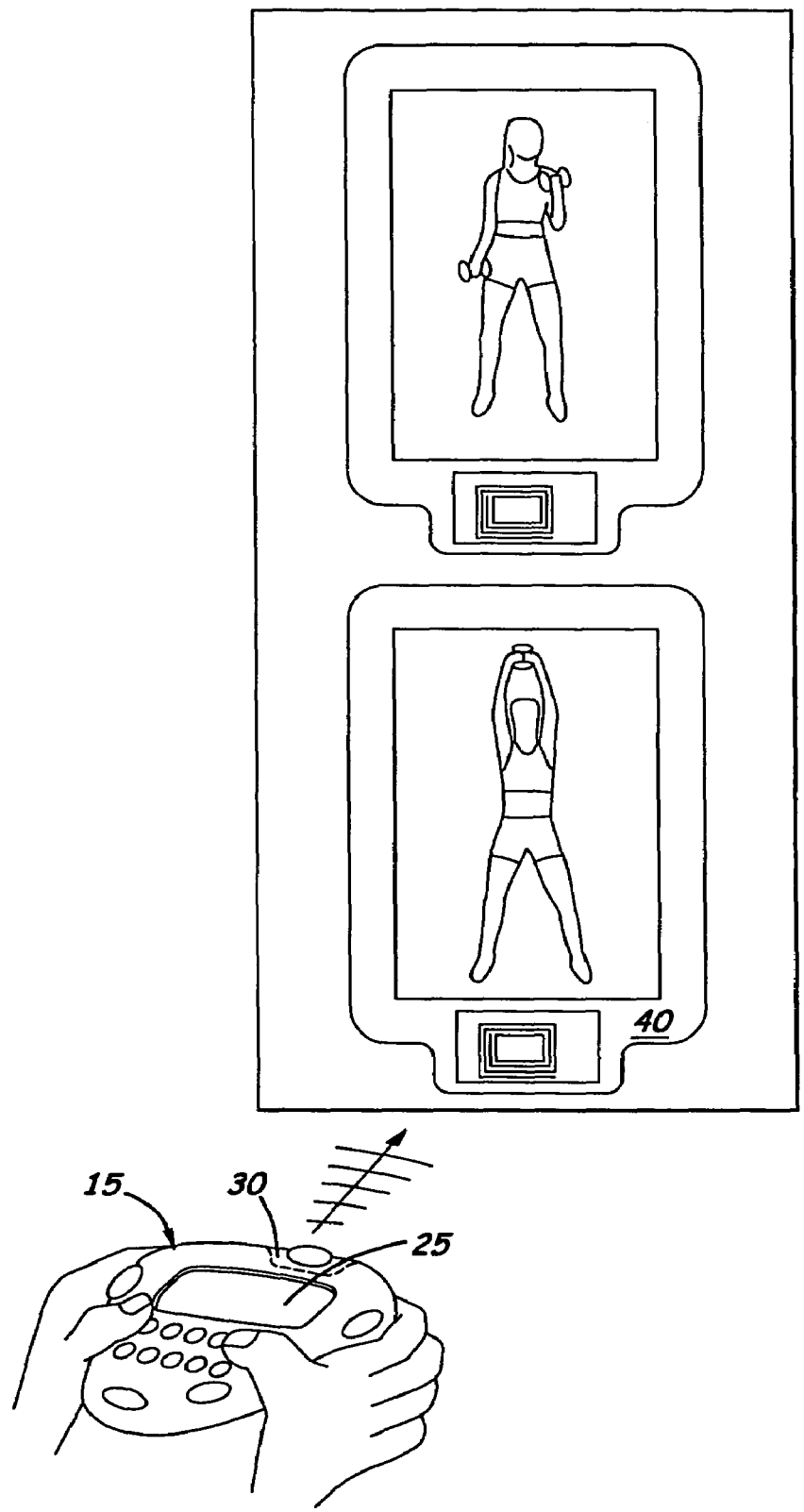
FIG. 2 is a perspective view of the handheld device being used to interrogate an EIDM.

Referring to the accompanying FIGS. 1-7, there is shown a system 10 for easily recording the exercise activities performed with or without exercise equipment that does not require the direct participation of a trainer. The system, denoted 5 includes a portable handheld device 15 shown more clearly in FIGS. 2 and 3, used to input exercise information that is uploaded to a local server 95. A fitness tools software program 50 loaded into the working memory of the local server 95 is used to collect the uploaded records from the handheld device 15 and store them in a permanent member data file 52. The member or authorized individuals can then use the fitness tools software program 50 to review the member data files to determine the member's fitness or training levels.

The handheld device 15 is lightweight, portable, and ruggedized to make it shock, heat, and moisture tolerant. Loaded into the memory of the handheld device 15 is an exercise data collection software program 35 that activates a built-in exercise identification module interrogation means, referred to as an EIDM interrogation means used to detect a unique EIDM attached to or located in the vicinity of the exercise activity data source. When the EIDM is interrogated, the exercise data collection software program 35 automatically executes a sub-routine 80-85 designed for the specific exercise activity data source 10 which sub-routine includes a date/clock function that automatically records start and stop times and the elapsed time for the exercise, as well as rest intervals between exercises. The sub-routines 80-85 presents one or more data entry pages 60A-60F with a plurality of prompts 61 displayed thereon each designed to sequentially elicit information manually inputted by the member into the handheld device 15. The exercise information is then stored in a temporary member data file 37 on the handheld device 15 that later is uploaded to a local server 95 via an uplink terminal, a wireless communication link or a hardwire connection. Each time the member moves to a new exercise activity data source 10, the EIDM interrogation means and EIDM are used to quickly identify the exercise activity data source 10 and present the proper exercise data entry page 60 and prompts 61 associated therewith.

The exercise data collection software program 37 automatically executes the specific sub-routine 80-85 associated with an identified exercise activity data sources 10A-10E (see FIG. 7). The exercise activity data source 10 may include a treadmill 10A, a stair machine 10B, an elliptical machine 10C, free weights 10D, or a weight machine 10E with a single or a plurality of weight stations as shown in FIG. 7. The exercise activity data source 10 may also be a weight lifting station, a basketball court, an aerobic exercise room, a stretching mat or room, a jump rope, a heart rate monitor, a blood pressure monitor, etc. (not shown). When the exercise activity data source 10 is recognized, the exercise data collection software program 35 automatically presents the exercise data page 60 that presents a plurality of prompts 61 suitable for the exercise activity data source 10.

The EIDM interrogation means and EIDM provide a communication link between the handheld device 15 and the exercise equipment. In the preferred embodiment, the EIDM interrogation utilizes an EIDM comprised of a computer chip, a chip housing ("can"), a pictorial representation of the exercise or activity which the subject EIDM is associated with and a "reader/receiver" incorporated within the handheld capable of powering and communicating with the EIDM via a physical contact. In other embodiments, the EIDM interrogation means may be a radio frequency identification device, hereinafter called a RFID, a magnetic decoder or a physical port connector. The EIDM is an ID tag 40, compatible with the EIDM interrogation means, such as a printed CCD identification label/hieroglyph, a barcode, a radio transducer, or magnetic strip or a port connector or other contact node capable of being detected or interrogated by the EIDM interrogation means.

The local server 95 is designed to receive uploaded temporary member data files 37 from the handheld device 15, use the fitness tools software program 50 to collect and store the member files in permanent member data file 52, and then use the fitness tools software program 50 to evaluate and present the information in the permanent member data file 52 to the member or authorized individuals. In a second embodiment of the system, shown in FIG. 2, the local server 95 is replaced by an uplink terminal that connects to a remote server located in or connected to a network operations center, NOC.

The Network Operations Center (NOC) provides a central repository for the system's database. In addition, the NOC provides a WAN presence to provide records access for club based fitness professionals working with the system's users. The NOC also provides the WAN presence by which auxiliary input to member records input can be made from sources outside of the gym (from home or "on the road"). The NOC also provides for system software updates, billing and other business functions associated with operation of the system, as well as network security and document security functions. These functions enable delivery of individual exercise records or WAN records access to authorized third parties with an interest in individual or group exercise records, including but not limited to: treating physicians, therapy professionals, NCAA and other athletic interests, Department of Defense (e.g. National Guard force readiness applications), corporate wellness incentive programs, etc.)

Figure 3:
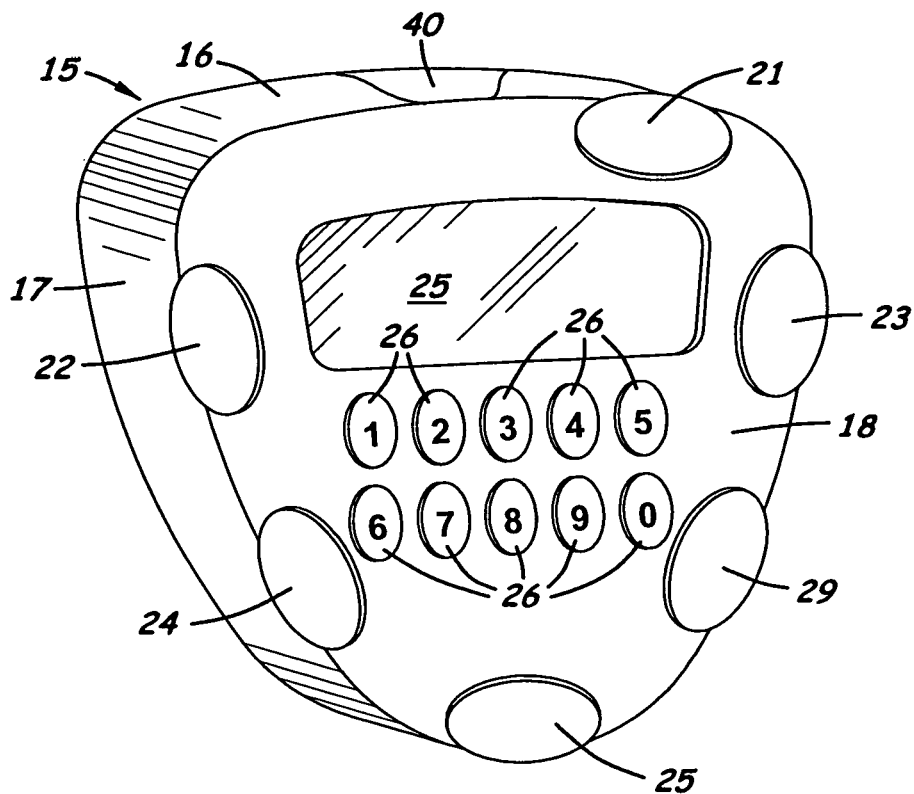
FIG. 3 is a front plan view of the handheld device.
Figure 4:
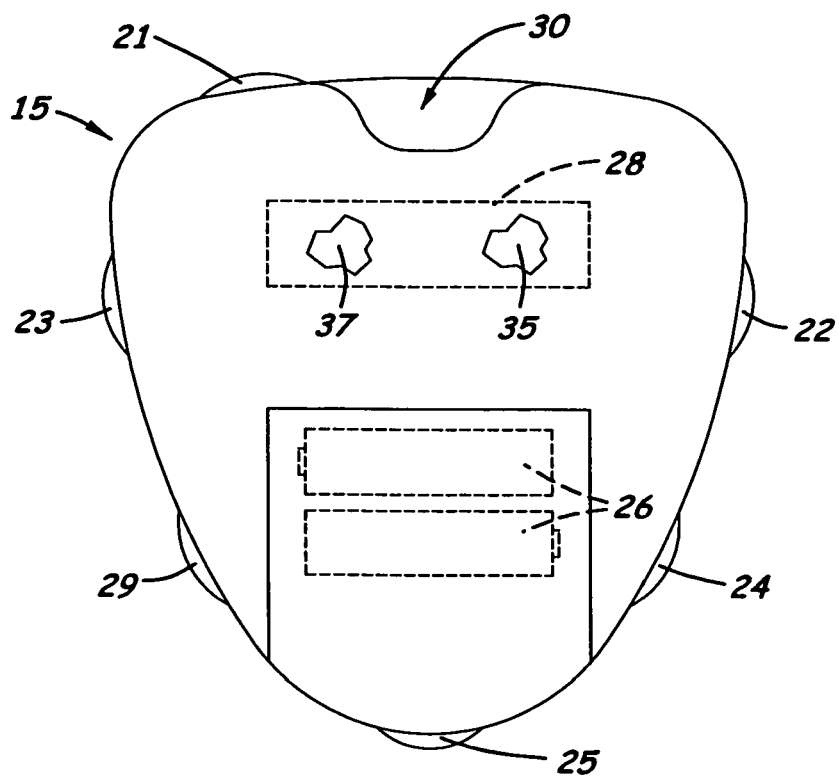
FIG. 4 is a rear plan view of the handheld device.
Figure 5:
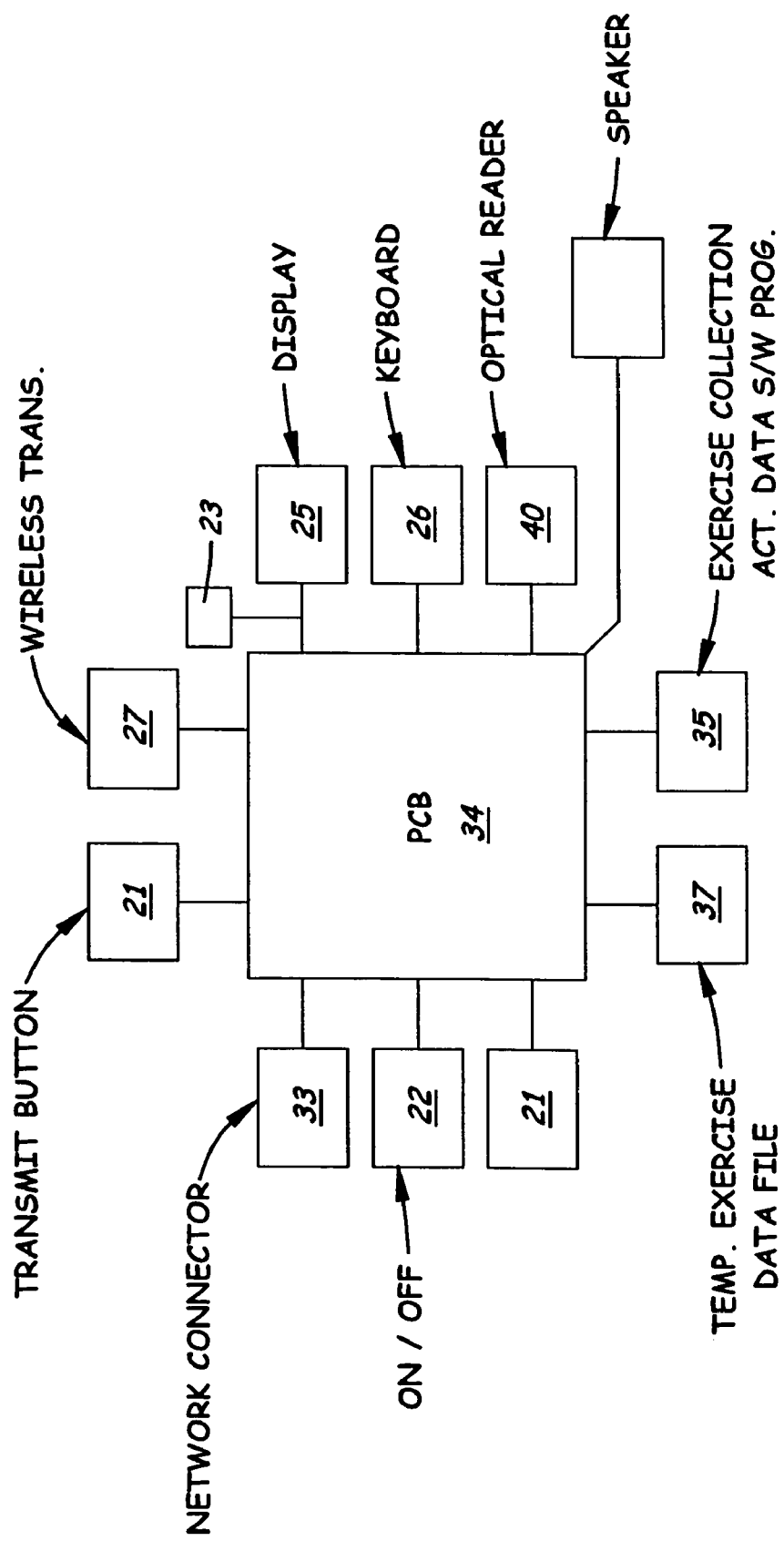
FIG. 5 is a block diagram of the handheld device

As shown in FIG. 3, the handheld device 15 includes a display monitor 25 and an input means. In the preferred embodiment, the input means is a set often numerical keys 26 located on the front surface 16 of the device 15. In other embodiments, the input means could be a combination monitor and "touch screen" functionality (not shown) with the ten numerical keys displayed thereon. Mounted inside the device 15 are batteries 28 (AA, AAA or 9 Volt) designed to supply a DC electric current. Mounted on the front surface 16 of the device is an "Identification" button 21. Mounted on the side surfaces 17 of the device 15 are a power switch 22 and an optional display monitor brightness switch 23. Mounted on the front surface 16 is a function key 24 and an optical reader activation button 21. Also, mounted on a side 17 or front surface 16 is a small speaker (not shown) to provide audible cues to a member, such as a cadence tone during certain exercises. Mounted on the rear surface 19 is an optional belt clip 24 or hook and loop connector pads (not shown). In other embodiments, a biometric security means, such as a fingerprint reader 25, may be included to prohibit inadvertent use of the handheld device by another member during the course of the exercise session. Also, mounted inside the device 15 is an optional wireless transmitter 27 enabling the device 15 to communicate with a wireless receiver 32 connected to the local server 95. The handheld device 15 may also include an optional network connection port 33 enabling the device 15 to communicate directly with the local server 95 or to the uplink terminal.

During use, the member activates the handheld device 15 and holds the optical reader 30 to read the ID tag 40 to interrogate and identify the fitness exercise activity data source 10. Once the fitness exercise activity data source 10 is identified, the exercise activity collection data software program 35, loaded into the handheld device's working memory, automatically auto-configures the device 15 and presents the proper exercise data page 60 for the fitness exercise activity data source 10. A representative exercise data sheet, shown in FIG. 6, is then presented on the display monitor 25.

On the exercise data page 60 is shown a plurality of prompts 61 that the member responds to after completion of the exercise activity. When the exercise activity is completed, the member manually inputs the data using the keys 26. The inputted exercise activity information is then stored in the temporary member file 37 for later uploading to the central server 95.

As more clearly shown in FIG. 7 each exercise activity data source (10A-10E shown) is assigned a sub-routine 80-84 that presents a specific exercise data page 60A-E to the display monitor 25. The nature of the prompts 61 may be the same or different. With some exercise equipment or activity, a second sub-routine 85 and a second specific exercise data sheet 60F are presented.

The permanent member data file 55 provides a comprehensive record of his or her cumulative exercise activity and achieved fitness level. This file 55 can then be evaluated and reviewed by club-based fitness professionals to provide a broad range of counseling services to members, and the record can be provided to medical professionals or other third parties away from the fitness center who may have legitimate interests in the fitness level of any particular member.

System Operation

The following operating scenario describes the exercise identification module interrogation means and the EIDM as an optical reader 30 and ID tag 40, respectively. It should be understood, however, that the optical reader 30 and ID tag 40 could be replaced with a radio frequency or infrared transmitter and receiver or other wireless or physical contact/hardwire transmitting and receiving devices for communication between the handheld device and the exercise activity data source's EIDM.

Prior to commencing the exercise activity, the member activates the EIDM component on the handheld. When the exercise activity data source 60 is identified, the sub-routine associated 80-84 with the exercise activity data source 10 is automatically executed. The exercise data page prompts 61 are then sequentially presented on the display monitor 25. The member enters data in response to prompts 61 displayed on the handheld device 15 for temporary storage in the handheld device 15 relative to the specific exercise. The member repeats this recording process for each exercise performed throughout the course of the exercise sessions. Upon completion of the exercise session, the temporary data files are uploaded into the member's permanent exercise activity file on the local central server 95. Alternatively, the handheld device is placed in the uplink terminal which automatically uploads the temporary data files to the member permanent files on a central server on the NOC. The fitness tools program is then used to review the permanent files and issue comments and recommendations to the member.

In summary, the method of collecting, transmitting, and recording an exercise routine comprising the following steps: (1) selecting an exercise activity data source each assigned a unique EIDM; (2) selecting a handheld device 15 including an exercise activity data collection software program 35 and an exercise identification module interrogation means, said exercise activity data collection software program 35 used to automatically execute a plurality of prompts 61 that request activity information for each unique EIDM and store the exercise activity information in a temporary member file 37; (3) connecting the handheld device to a server 95 and uploading the data in the temporary member file to a permanent member file; (4) loading a fitness tools software program 50 into said server 95, said fitness tools program 50 used to evaluate and review the data in the permanent member file 37 to determine the fitness level of a member and recommend future exercises.

While a preferred embodiment of the exercise recording system has been described in detail, it should be apparent that modifications and variations thereto are possible, all of which fall within the true spirit and scope of the invention. With respect to the above description then, it is to be realized that the optimum dimensional relationships for the components of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. For example, the term "exercise activity data source" is used to encompass every exercise equipment activity or non-equipment activity. The term "wireless communication link and EIDM" are meant to encompass all means of wireless communication in which an exercise activity is recognized by the handheld device.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A physical exercise records system, comprising:
  a. a plurality of exercises activity data sources;
  b. a unique identifying EIDM associated with each said exercise activity data source;
  c. a handheld device including a processor with working memory, an input means, a display means, and an EIDM interrogation means used to identify and interrogate a plurality of said EIDMs each associated with an exercise activity data source, and;
  d. an exercise software program loaded into said working memory of said handheld device, said program including a plurality of sub-routines each associated with one said EIDM, said exercise software program presents an exercise data entry page after said EIDM is identified and interrogated on said display means that queries a user to input exercise activity data relevant to the exercise activity data source.

2. The physical exercise records system, as recited in claim 1, wherein said EIDM interrogation means and said EIDM is a optical reader and a compatible tag element capable of being interrogated by said optical reader.

3. The physical exercise records system, as recited in claim 1, wherein said EIDM interrogation means and said EIDM is a RFID reader and compatible tag element.

4. The physical exercise records system, as recited in claim 1, further including a server capable of receiving the input records from said handheld device.

5. The physical exercise records system, as recited in claim 1, further including a tool set software program.

6. The physical exercise records system, as recited in claim 1, further including a network operation center capable of receiving input records from said handheld device.

7. The physical exercise records system, as recited in claim 1, further including a wireless communication link between handheld device and said server.

8. The physical exercise records system, as recited in claim 1, wherein said EIDM interrogation means is a physical connector.

9. An exercise facility exercise recording system, comprising:
   a. a plurality of exercise activity data sources;
   b. an identifying EIDM attached to or in the vicinity of each said exercise activity data source;
   c. a handheld device including an EIDM interrogation means capable of communication with, identifying and interrogating a plurality of said EIDM associated with said exercise activity data sources, said handheld device also including a display monitor and a data input means; and,
   d. an exercise software program loaded into said handheld device, said program being automatically executed after said EIDM is identified and interrogated to present at least one of a plurality of sub-routines each associated with said exercise activity data source attached or in the vicinity of said EIDM, each said sub-routine presents one or more display screens requesting specific exercise data inputted by the user regarding the exercise performed using said exercise activity data source.

10. A method for recording and monitoring exercise activities by users of an exercise facility that contains a plurality of exercise activity data sources each associated with an identifiable EIDM, said exercise facility includes a central server with a member data file created therein for each user and a fitness tools program loaded therein capable of receiving information from a plurality of handheld devices operated within said exercise facility, each said handheld device includes a EIDM interrogation means used to identify and interrogate the EIDM associated with the exercise activity data sources in the exercise facility and a software program that executes a EIDM specific sub-routine that requests specific exercise performed at exercise activity data source to be manually inputted into the handheld device, said method comprising:
   a. selecting a handheld device that includes a EIDM interrogation means for identify and interrogating each said EIDM associated with said exercise activity data sources, a display monitor, a data input means, and an exercise software program capable of executing a EIDM specific sub-routine that presents a plurality of queries requesting the input of data pertaining to the exercise performed with said exercise activity data source;
   b. selecting an exercise activity data source in the exercise facility with an EIDM associated therewith;
   c. using said EIDM interrogation means to identify and interrogate EIDM associated with said exercise activity data source;
   d. using said input means on said handheld device inputting data into said handheld device in response to queries presented by a specific sub-routine on said display monitor on said handheld device;
   e transmitting said exercise data from said handheld device to said central server; and,
   f. operating said fitness tool program to process said exercise data from said handheld device.

* * * * *